United States Patent [19]

Baumann et al.

[11] 4,197,255
[45] Apr. 8, 1980

[54] METHOD FOR THE PRODUCTION OF BLEACHED, LOW-SULTONE OLEFIN SULFONATES

[75] Inventors: Horst Baumann, Leichlingen; Manfred Teupel, Langenfeld, both of Fed. Rep. of Germany

[73] Assignee: Henkel Kommanditgesellschaft auf Aktien (Henkel KGaA), Dusseldorf, Fed. Rep. of Germany

[21] Appl. No.: 892,423

[22] Filed: Mar. 31, 1978

Related U.S. Application Data

[63] Continuation of Ser. No. 735,889, Oct. 26, 1976, abandoned.

[30] Foreign Application Priority Data

Oct. 27, 1975 [AT] Austria .................................. 8158/75

[51] Int. Cl.$^2$ ............................................. C07C 139/14
[52] U.S. Cl. .................................................. 260/513 T
[58] Field of Search .................................... 260/513 T

[56] References Cited

U.S. PATENT DOCUMENTS

| 3,639,282 | 2/1972 | Sharman | 260/513 T |
| 3,997,575 | 12/1976 | Ogoshi et al. | 260/513 T |
| 4,052,431 | 10/1977 | Baker et al. | 260/513 T |

FOREIGN PATENT DOCUMENTS 983056 2/1965 United Kingdom ................ 260/513 T

OTHER PUBLICATIONS

Cotton et al., "Advanced Inorganic Chemistry", pp. 565–574 (1966).

Primary Examiner—Nicky Chan
Attorney, Agent, or Firm—Hammond & Littell, Weissenberger & Muserlian

[57] ABSTRACT

Aqueous solutions of alkali metal $C_{8-22}$ α-olefin sulfonates of light color and of low sultone content are prepared rapidly and at moderate temperatures by:
(a) reacting a $C_{8-22}$ α-olefin with gaseous sulfur trioxide thereby forming a crude sulfonation product mixture containing $C_{8-22}$ olefin sulfonic acids, with a content of sultones,
(b) bleaching said crude sulfonation product mixture at 30° C. to 80° C. for 10 to 60 minutes with an aqueous alkaline bleaching solution at a pH of at least 8,
(c) heating said diluted bleached sulfonation product mixture containing excess alkali to a temperature of from 140° C. to 170° C. until the sultone content of said sulfonation product mixture is less than 100 ppm, and
(d) recovering said alkali metal $C_{8-22}$ α-olefin sulfonates of light color and of low sultone content. A decrease in the sultone content from as much as 650,000 ppm to less than 50 ppm is possible by the method.

10 Claims, No Drawings

METHOD FOR THE PRODUCTION OF BLEACHED, LOW-SULTONE OLEFIN SULFONATES

This is a continuation of Ser. No. 735,889, filed Oct. 26, 1976, and now abandoned.

RELATED ART

Surface-active α-olefin sulfonates are customarily produced technically by sulfonating linear α-olefins having 8 to 22 carbon atoms at temperatures of between 20° C. to 100° C. with gaseous sulfur trioxide which is diluted with inert gases, such as air or nitrogen, to a concentration of 0.5% to 20% by volume. The sultones formed by an addition reaction to the alkene sulfonic acids formed during sulfonation are hydrolyzed subsequent to sulfonation in which case, usually excess alkali and temperatures of between 80° C. and 200° C., especially 100° C., are employed. The sulfonation products and consequently the sulfonates so produced are, however, too dark in color for most purposes, and therefore they are usually cleaned or bleached before being used further.

According to British Patent Specification No. 983,056, bleaching is effected with hydrogen peroxide, alkali metal chlorites or alkali metal hypochlorites or even the components for forming these compounds, the bleaching being effected before, during or subsequent to the hydrolysis of the sultones. The bleaching may be performed either on the crude acid sulfonation product or on the hydrolyzate which may be acidic, alkaline or neutral. Particularly good bleaching is obtained when the bleaching step is performed subsequent to alkaline hydrolysis, and when hypochlorites or chlorites are used for the purpose.

It has now been shown that the olefin sulfonates produced in this manner still contain some quantities of sultones. However, after Druckrey et al ascertained carcenogenic properties in propane sultone in the Cancer Research Journal, 75, 69–84 (1970), serious toxicological objections to sultone-containing olefin sulfonates or their use in detergents and wash liquids have been raised recently. These objections are exclusively directed against the sultone admixtures since low-sultone α-olefin sulfonates are of considerable technical interest because of their good biodegradability, their comparatively favorable skin-compatibility, and their excellent cleaning properties.

One current way of hydrolyzing the difficultly saponifiable sultones completely is to make the hydrolysis temperature as high as possible, such as by operating under pressure at temperatures of above 170° C. to 180° C. However, olefin sulfonates hydrolyzed in this temperature range are generally very dark in color, so that bleaching cannot be avoided before they are used further. Unfortunately, however, even an olefin sulfonate which has been hydrolyzed at appropriately high temperatures and has subsequently been bleached still always has a remarkably high-sultone content.

OBJECTS OF THE INVENTION

An object of the present invention, therefore, is to develop a method which eliminates the disadvantages mentioned and makes it possible to produce an attractive product which, at the same time, is toxicologically harmless.

Another object of the invention is the development of a process for the production of a light-colored olefin sulfonate having low sultone content comprising the steps of (a) reacting a $C_{8-22}$ α-olefin with from 1.0 to 1.5 mols of gaseous sulfur trioxide diluted with an inert gas to a concentration of 0.5 to 20% by volume, thereby forming a crude sulfonation product mixture comprising a $C_{8-22}$ olefin sulfonic acid, with a content of sultones, (b) diluting said crude sulfonation product mixture to a 5% to 80% by weight solution and bleaching said aqueous solution containing the crude sulfonation product mixture at 30° C. to 80° C. for 10 to 60 minutes at a pH of over 8 by the action of an inorganic bleaching agent equivalent to 0.5% to 5% by weight, based on the olefin sulfonate content, of NaOCl, selected from the group consisting of active oxygen bleaching agents and active chlorine bleaching agents, (c) heating said diluted bleached sulfonation product mixture containing excess alkali sufficient to give an alkaline pH after hydrolysis is completed, at a temperature of from 140° C. to 170° C. for a time sufficient until the sultone content of the sulfonation product mixture is less than 100 ppm, and (d) recovering said light-colored olefin sulfonate having low-sultone content.

These and other objects of the invention will become more apparent as the description thereof proceeds.

DESCRIPTION OF THE INVENTION

The present invention provides a method of producing light-colored low-sultone olefin sulfonates by reacting olefins containing 8 to 22 carbon atoms and a terminal double bond with 1.0 to 1.5 times the molar quantity of gaseous sulfur trioxide, diluted with inert gas to a concentration of 0.5% to 20% by volume, bleaching the sulfonation products with hydrogen peroxide, alkali metal chlorites or alkali metal hypochlorites or the components forming these substances in situ and hydrolyzing the sulfonation products, characterized in that the crude sulfonation products are bleached in aqueous-alkaline 5% to 80% by weight solution at a temperature of 30° C. to 80° C. for a period of 10 to 60 minutes with a quantity of bleaching agent, which is, relative to the olefin sulfonate content, equivalent to 0.5% to 5% by weight of NaOCl in bleaching power, the mixture thereupon being heated to a temperature of 140° C. to 170° C., preferably 150° C. to 165° C., in the presence of an excess quantity of alkali relative to the hydrolyzed end product, and being left at this temperature until the sultone content has dropped to less than 100 p.p.m., preferably below 50 p.p.m.

More particularly, the present invention involves a process for the production of a light-colored olefin sulfonate having low-sultone content comprising the steps of (a) reacting a $C_{8-22}$ α-olefin with from 1.0 to 1.5 mols of gaseous sulfur trioxide diluted with an inert gas to a concentration of 0.5 to 20% by volume, thereby forming a crude sulfonation product mixture comprising a $C_{8-22}$ olefin sulfonic acid, with a content of sultones, (b) diluting said crude sulfonation product mixture to a 5% to 80% by weight solution and bleaching said aqueous solution containing the crude sulfonation product mixture at 30° C. to 80° C. for 10 to 60 minutes at a pH of over 8 by the action of an inorganic bleaching agent equivalent to 0.5% to 5% by weight, based on the olefin sulfonate content, of NaOCl, selected from the group consisting of active oxygen bleaching agents and active chlorine bleaching agents, (c) heating said diluted bleached sulfonation product mixture containing excess alkali sufficient to give an alkaline pH after hydrolysis is completed, at a temperature of from 140° C. to 170° C. for a time sufficient until the sultone content of the sulfonation product mixture is less than 100 p.p.m., and (d) recovering said light-colored olefin sulfonate having low-sultone content.

In the sulfonation the amount of sulfur trioxide reacted is preferably 1.05 to 1.15 mol per mol of the α-olefin.

The crude product of the sulfonation step typically is composed of about 55%–65% (averaging about 60%) of sultones, about 2% to 10% (averaging about 5%) of disulfonic acids, and 30%–40% (averaging 35%) of monosulfonic acids. The proportion of disulfonic acids increases with the amount of sulfur trioxide which is admitted as reagent. It is this mixture which is purified by the process of the present invention. The process of the present invention, however, is applicable to sulfonation products containing as little as 100,000 ppm of sulfones.

Preferably, in the above process, the bleaching is continued until the color of the solution remains substantially constant, i.e., until the bleaching action of the bleaching component of the solution is substantially complete.

We have further found that the sultone content can be decreased from above 650,000 p.p.m. to below 50 p.p.m. with production of an olefin sulfonate of excellent light color sufficiently rapidly to permit performance of the process in continuous manner.

The first step (subsequent to the sulfonation of the olefin) of the method according to the invention is the alkalization of the crude sulfonation product with aqueous alkali. The pH value of the solution thereby formed should be at least 8, and preferably should be 10 to 14, and should be maintained above 8 (and preferably in the range of 10 to 14) during bleaching. The sulfonation product may be stirred into the aqueous alkali solution, and a sufficient excess of alkalis should be used so that the solution is alkaline at a pH of at least 8 after hydrolysis and bleaching (i.e., the amount of alkali should be in excess of the stoichiometrical). Another method which may be employed comprises adding initially only a portion of the total alkali needed and adding the remainder together with the bleaching agent. If preferred, the excess alkali needed for the hydrolysis of the sultones can be added after bleaching. The latter method, however, requires an additional step and is, therefore, less advantageous. Suitable alkalis are the strongly alkaline alkali metal hydroxides, carbonates, silicates and phosphates. Preferably the alkali metal is sodium and potassium. Sodium hydroxide is preferred.

The concentration of the aqueous sodium hydroxide and the quantity of the water to be introduced, where applicable, with the bleaching agent, are such that the concentration of the olefin sulfonate is 5% to 80%, preferably 20% to 60%, by weight.

The temperature during neutralization and subsequent bleaching should not exceed 80° C. and the mixture should be cooled or precooled when aqueous sodium hydroxide or other exothermic alkali is added.

The second step in the method according to the invention comprises bleaching the alkalized sulfonation mixture. Any suitable water-soluble inorganic oxidizing bleach can be used which is stable at an alkali pH. Suitable bleaching agents for the purpose are active oxygen bleaches, such as hydrogen peroxide, sodium peroxide, peroxides producing perhydrates and hydrogen peroxide and active chlorine bleaches, such as alkali metal hypochlorites, alkali metal chlorites, chlorine, and chlorine dioxide, the latter two reacting with the excess alkali to form alkali metal hypochlorites or chlorites. Alkali hypochlorites or chlorine introduced into the alkaline mixture in gaseous form or as aqueous chlorine solution, are preferably used because of their cheapness, absence of toxicity and effectiveness. In the latter case, an appropriate consumption of alkali is to be taken into consideration.

Depending upon the degree of discoloration of the substrate and the amount of bleaching desired, in the case of hypochlorites, the quantity of bleaching agent added generally falls within the range of 0.5% to 5%, and preferably 1% to 3%, by weight, calculated as NaOCl based on the weight of sulfonation product present. Other bleaching agents are added in equivalent amounts.

Bleaching is effected at temperatures of 30° C. to 80° C., preferably 50° C. to 60° C. In the preferred temperature range, the bleaching is substantially complete in 15 to 30 minutes. Higher temperatures result in slightly faster bleaching, and lower temperatures require a slightly longer time. It is advisable to stir the reaction mixture intensively during the bleaching treatment. As stated, the pH should be in excess of 8 during the bleaching. The necessary alkali can be added at the start of the bleaching step, or the minimum amount needed to adjust the solution to pH 8 can be added at the outset and the pH maintained above 8 by periodic small additions.

It is preferable for the superalkalization and bleaching to be effected in a single step, whereby an aqueous sodium hydroxide solution containing bleaching agent is used, the appropriate quantity of the acid sulfonation mixture is stirred in and the bleaching treatment is continued by stirring until the desired degree of lightness is reached or the precalculated quantity of bleaching agent is consumed.

For hydrolysis—the third step in the method according to the invention—the bleached sulfonation mixture containing excess alkali is heated in a pressure vessel to temperatures of 140° C. to 170° C., preferably 150° C. to 165° C. Hydrolysis is continued until the sultone content has dropped by at least 90%, i.e., to less than 100 ppm, preferably less than 50 ppm, based on the weight of the solution. Depending upon the hydrolysis temperature chosen, only 10 to 30 minutes are needed therefor. About 25 minutes are needed as a rule at 150° C., and only about 15 minutes are needed at 165° C. Longer hydrolysis times at higher temperatures should be avoided, since they do not notably improve the hydrolysis result and cause deterioration of color. The excess alkali used prior to hydrolysis should be such that the solution after hydrolysis has been completed is still alkaline, i.e., has a pH of at least 9, preferably 11 to 14. The addition of alkali to produce this result is termed "superalkalization."

The method may be carried out in batches or continuously, though in the latter case a diffusion apparatus fitted with pumps, dosing means and feeding means is used and hydrolysis is effected, for example, in a heated spiral tube, the diffusion being regulated so that the specified mean reaction times are observed.

After hydrolysis has been completed, the solution is cooled; pressure is released, and the solution is neutralized, preferably with sulfuric acid.

The resulting solution may be processed further immediately to form detergents, wash liquids or cleansers. The sulfonates can be recovered in dry particulate free-flowing form by drum drying or, preferably, by spray-drying the solution.

The olefin sulfonates obtained are distinguished by a light color and low sultone content. This sultone content is on average lower by the factor 100 (i.e., it is about 1%) of the sultone content of olefin sulfonates which have been hydrolyzed and bleached according to known methods.

The sultone content of the product can be determined as follows:

10 Grams of olefin sulfonate are dissolved in 100 ml of a 1:1 water/ethanol mixture and are extracted with n-hexane. The hexane fraction is removed and the hexane is allowed to evaporate. The residue is dissolved in chloroform and the resulting solution is poured into a chromatographic column column charged with a weighed quantity of silica gel and the eluate is evaporated until the residue is dry.

The sultone contained in the residue may be determined quantitatively by saponifying the sultone completely and performing a two-phase titration of the sulfonates thereby formed with hyamine solution (a quaternary ammonium cationic surfactant; see U.S. Pat. No. 2,115,250) against a mixed indicator.

A quick qualitative determination is possible by thin-layer chromatography on silica gel and dyeing with 4-(4-nitrobenzyl)-pyridine.

The invention is further described by the examples which follow. These examples are best embodiments of the invention and are not to be construed as limitative thereof.

EXAMPLES 1 TO 3

A linear $C_{14}$–$C_{18}$ olefin of which 80% was of $C_{16}$ chain length and wherein the double bonds were terminal was used as the starting material. It was continuously sulfonated in a thin-layer reactor with 1.1 mol of sulfur trioxide, which was present in 3% by volume dilution with air at a temperature of 32° C. The extent of sulfonation (determined by saponification) was 95.7%.

Samples of this crude sulfonation mixture were hydrolyzed and bleached under various conditions, as shown in the following table. Hydrolysis and bleaching were effected after the addition of 1.2 times the molar quantity of sodium hydroxide as a 30% aqueous solution. NaOCl was added as bleach in the form of an aqueous solution containing 13% active chlorine by weight. The bleaching was for 25 minutes at 60° C. (Hydrolysis and bleaching in at acid pH values were omitted since this procedure produces products which are distinctly darker in color and are, therefore, less useful). The pH value of the solution was 14 (at 20° C.) during bleaching and also after the conclusion of hydrolysis.

The sultone content of the resulting solutions was determined quantitatively by the method described above. The color values of the solutions were determined in a 4" tube by use of the Lovibond tintometer after dilution of the solutions to a sulfonic content of 5% by weight.

The comparative tests are designated by letters.

The examples which illustrate the present invention are designated by numbers. Test series A utilizes unbleached sulfonates. Test series B utilizes sulfonates bleached after hydrolysis. Test series C utilizes sulfonates bleached prior to hydrolysis, and test series D utilized sulfonates simultaneously hydrolyzed and bleached. One solution was treated for 3 hours at 100° C. and the other was treated for 10 minutes at 180° C.

TABLE

| Test | Treatment Steps | Hydrolysis °C. | Hydrolysis Length | Residual Sultone Content p.p.m.* | Lovibond Color Number Yellow | Red | Blue |
|---|---|---|---|---|---|---|---|
| A | Alkali hydrolyzed (unbleached) | 100 | 3 hrs. | 1,600 | 4 | 1 | 0 |
| A' | | 180 | 10 min. | 25 | 5 | 2 | 0 |
| B | Alkali hydrolyzed bleached afterwards with 2% NaOCl | 100 | 3 hrs. | 1,800 | 1 | 0 | 0 |
| B' | | 180 | 10 min. | 550 | 2 | 0.4 | 0 |
| C | Bleached with 2% NaOCl, then alkali hydrolyzed | 100 | 3 hrs. | 1,500 | 3 | 1 | 0 |
| C' | | 180 | 10 min. | 20 | 4 | 2 | 0 |
| D | Simultaneously alkali hydrolyzed and bleached with 2% NaOCl | 100 | 3 hrs. | 700 | 1 | 0 | 0 |
| D' | | 180 | 10 min. | 60 | 6 | 1.2 | 0 |
| 1 | Superalkalized, bleached with 2% NaOCl, hydrolyzed | 150 | 25 min. | 50 | 1 | 0.2 | 0 |
| 2 | | 160 | 20 min. | 30 | 2 | 0.2 | 0 |
| 3 | | 165 | 15 min. | 20 | 2 | 0.3 | 0 |

*Parts per million by weight in the olefin sulfonate.

The olefin sulfonate solutions produced by the process of the present invention are distinguished by a sultone content of a maximum of 50 p.p.m. and by Lovibond color values of less than 3 for yellow, less than 0.4 for red, and 0 for blue. Solutions produced by other processes are unacceptably dark in color or have too high a sultone content or have both disadvantages.

The results show that the above process is capable of rapidly decreasing the sultone content of the solution by more than 98% with production of a very light colored solution.

EXAMPLE 4

The procedure of Example 3 is repeated except that the sodium hypochlorite solution added is replaced by aqueous hydrogen peroxide solution of equivalent bleaching strength. The results are substantially the same.

The preceding specific embodiments are illustrative of the practice of the invention. It is to be understood, however, that other expedients known to those skilled in the art, or disclosed herein, may be employed without departing from the spirit of the invention or the scope of the appended claims.

We claim:

1. A process for the production of alkali metal $C_{8-22}$ α-olefin sulfonates of light color and of low sultone content comprising:
   (a) reacting a $C_{8-22}$ α-olefin with 1.0 to 1.5 mols of gaseous sulfur trioxide diluted with an inert gas to a concentration of 0.5% to 20% by volume thereby forming a crude sulfonation product mixture containing a $C_{8-22}$ olefin sulfonic acid, with a content of sultones,
   (b) diluting said crude sulfonation product mixture to a 5% to 80% by weight solution and bleaching said crude sulfonation product mixture at 30° C. to 80° C. for 10 to 60 minutes with an aqueous alkaline bleaching solution, said bleaching step being conducted at a pH of from 10 to 14, the bleaching being effected by the action of a water-soluble, inorganic bleaching agent which is stable at an alkali pH selected from the group consisting of alkali metal hypochlorites and chlorine, the amount of said bleaching agent being equivalent to 0.5% to 5% by weight, based on the olefin sulfonate content, of NaOCl,
   (c) heating said diluted bleached sulfonation product mixture containing excess alkali to a temperature of from 140° C. to 170° C. for a time sufficient until the sultone content of the sulfonation product mixture is less than 100 ppm, where the pH after hydrolysis is complete, is at least 9, and
   (d) recovering said alkali metal $C_{8-22}$ α-olefin sulfonates of light color and of low sultone content.

2. The process of claim 1 wherein said heating to a temperature of from 140° C. to 170° C. of step (c) is for a period of from 10 to 30 minutes.

3. The process according to claim 1 wherein said inorganic bleaching agent is sodium hypochlorite.

4. The process according to claim 1 wherein the weight of said bleach is equivalent to 1% to 3% by weight, based on the olefin sulfonate content of NaOCl.

5. The process according to claim 1 wherein said crude sulfonation product mixture is diluted to a 20% to 60% by weight solution.

6. The process according to claim 1 wherein in Step (b) the temperature during said bleaching is 50° C. to 60° C.

7. The process according to claim 1 wherein in Step (c) the temperature at which solution is heated is 150° C. to 165° C.

8. The process according to claim 1 wherein the pH after hydrolysis is complete in Step (c) is in the range of 11 to 14.

9. The process according to claim 1 wherein said heating Step (c) is continued until the sultone content is less than 50 p.p.m.

10. A process according to claim 1 whereas the amount of said sulfur trioxide is 1.05 to 1.15 mol per mol of said α-olefin.

* * * * *